US011450428B2

(12) United States Patent
Soreefan et al.

(10) Patent No.: US 11,450,428 B2
(45) Date of Patent: Sep. 20, 2022

(54) TEMPERATURE MONITORING SYSTEMS AND METHODS FOR DETERMINING A CHANGE IN TEMPERATURE OF TARGET AREAS

(71) Applicant: Hill-Rom Services, Inc., Batesville, IN (US)

(72) Inventors: Ibne Soreefan, West Chester, OH (US); Tyler Holmes, Rochester, NY (US); John Lane, Weedsport, NY (US); Eric Agdeppa, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 196 days.

(21) Appl. No.: 16/589,173

(22) Filed: Oct. 1, 2019

(65) Prior Publication Data

US 2020/0105407 A1 Apr. 2, 2020

Related U.S. Application Data

(60) Provisional application No. 62/740,258, filed on Oct. 2, 2018.

(51) Int. Cl.
*G16H 40/63* (2018.01)
*A61B 5/00* (2006.01)
(Continued)

(52) U.S. Cl.
CPC ........... *G16H 40/63* (2018.01); *A61B 5/0008* (2013.01); *A61B 5/0075* (2013.01);
(Continued)

(58) Field of Classification Search
CPC ............................... A61B 5/015; G01J 5/0025
See application file for complete search history.

(56) References Cited

U.S. PATENT DOCUMENTS 9,750,414 B2 9/2017 Lane et al.
2004/0254472 A1* 12/2004 McQuilkin ............ A61B 5/015
600/473
(Continued)

FOREIGN PATENT DOCUMENTS

EP 1646310 B1 7/2015
EP 3336498 A1 6/2018
JP S5462880 A 5/1979

OTHER PUBLICATIONS

Extended European Search Report for European Application No. 19200913.2 dated Mar. 4, 2020, 11 pages.
(Continued)

*Primary Examiner* — Fabricio R Murillo Garcia
(74) *Attorney, Agent, or Firm* — Dinsmore & Shohl LLP

(57) ABSTRACT

A monitoring system that includes an infrared detector comprising a field of view that detects temperature data from the field of view and provides a signal indicative of at least a detected temperature of a subject. The system includes a tab comprising a tab temperature that is positioned within the field of view such that the infrared detector detects the tab and emits a signal indicative of a detected temperature of the tab. The system includes a temperature sensor secured to the tab that detects the tab temperature and provides a signal indicative of a reference temperature. A control unit is communicatively coupled to the infrared detector and the temperature sensor and computes a net value between the detected temperature of the subject and the detected temperature of the tab. The control unit calculates a core temperature of the subject by combining the net value with the reference temperature.

20 Claims, 7 Drawing Sheets

(51) Int. Cl.
 *A61B 5/11* (2006.01)
 *G08B 21/04* (2006.01)
(52) U.S. Cl.
 CPC ........ *A61B 5/1115* (2013.01); *G08B 21/0423* (2013.01); *G08B 21/0461* (2013.01)

(56) References Cited

U.S. PATENT DOCUMENTS

| | | |
|---|---|---|
| 2007/0153871 A1 | 7/2007 | Fraden |
| 2012/0057614 A1* | 3/2012 | Normann ................ G01K 3/02 |
| | | 374/112 |
| 2013/0116573 A1* | 5/2013 | Herman ................ A61B 5/444 |
| | | 600/474 |
| 2017/0035302 A1 | 2/2017 | Mullin et al. |
| 2020/0232683 A1* | 7/2020 | Shingu .................. B61D 27/00 |

OTHER PUBLICATIONS

Chinese Patent Office; First Office Action for Appln. Serial No. CN 01910940236.6; dated Dec. 27, 2021; 16 Pgs.
European Office Action for European Application No. 19200913.2 dated Jul. 4, 2022, 7 pages.

* cited by examiner

TEMPERATURE MONITORING SYSTEMS AND METHODS FOR DETERMINING A CHANGE IN TEMPERATURE OF TARGET AREAS

CROSS-REFERENCE TO RELATED APPLICATIONS

The present disclosure claims the benefit of U.S. Provisional Patent Application Ser. No. 62/740,258 filed Oct. 2, 2018 and entitled "Temperature Monitoring Systems and Methods for Determining a Change in Temperature of Target Areas," the entirety of which is incorporated by reference herein.

FIELD

The present disclosure generally relates to temperature monitoring systems and, in particular to temperature monitoring systems which include temperature reference tabs for improving temperature detection accuracy, and methods for utilizing the same to determine a temperature of target areas.

TECHNICAL BACKGROUND

Various systems may be used in health care facilities to track a subject's condition and detect changes in the subject's condition for prompt attention and care. Such systems may generally include a detector or camera that monitors the subject as the subject is positioned in the care room. The system may notify a caregiver of a change in the subject's condition.

Systems using infrared cameras may be used to monitor the subject's temperature by capturing thermal radiation emitted by the subject. Such systems may include signal noise intrinsic to the imaging sensor technology of the camera that reduces the accuracy of the detected temperatures. For example, in conventional infrared cameras, the measured temperatures may have an error range of ±4° Celsius. However, such error ranges may be too large to accurately detect meaningful changes in the temperature of a subject.

Accordingly, a need exists for alternative temperature monitoring systems with increased measurement accuracy.

SUMMARY

According to a first aspect A1, a monitoring system, comprises: an infrared detector comprising a field of view, the infrared detector detecting temperature data from the field of view and providing a signal indicative of at least a detected temperature of a subject within the field of view; a tab comprising a tab temperature, wherein the tab is at least partially positioned within the field of view of the infrared detector such that the infrared detector detects the tab and emits a signal indicative of a detected temperature of the tab; a temperature sensor secured to the tab, the temperature sensor detecting the tab temperature and providing a signal indicative of a reference temperature; and a control unit communicatively coupled to the infrared detector and the temperature sensor, the control unit comprising a processor and a non-transitory memory device comprising computer readable and executable instructions that, when executed by the processor, cause the control unit to: compute a net value between the detected temperature of the subject and the detected temperature of the tab; and calculate a core temperature of the subject by combining the net value with the reference temperature.

A second aspect A2 includes the monitoring system of the first aspect, wherein the core temperature of the subject calculated by the control unit is within ±0.5° Celsius of an actual temperature.

A third aspect A3 includes the monitoring system of any of the first through second aspects, further comprising a remote station, wherein the control unit is coupled to the remote station.

A fourth aspect A4 includes the monitoring system of any of the first through third aspects, wherein the computer readable and executable instructions, when executed by the processor, transmit a signal indicative of the core temperature to the remote station.

A fifth aspect A5 includes the monitoring system of any of the first through fourth aspects, wherein the remote station receives the signal indicative of the core temperature from the control unit and determines a variance between the core temperature of the subject and a baseline temperature of the subject.

A sixth aspect A6 includes the monitoring system of any of the first through fifth aspects, wherein the baseline temperature is an initial core temperature determined by the monitoring system and stored in the remote station at initialization of the monitoring system.

A seventh aspect A7 includes the monitoring system of any of the first through sixth aspects, wherein the baseline temperature is input into the remote station by an operator.

An eighth aspect A8 includes the monitoring system of any of the first through seventh aspects, wherein the remote station emits an alarm signal when the variance between the core temperature of the subject and the baseline temperature of the subject is greater than a threshold.

A ninth aspect A9 includes the monitoring system of any of the first through eighth aspects, wherein the alarm signal is transmitted from the remote station to a handheld device.

A tenth aspect A10 includes the monitoring system of any of the first through ninth aspects, wherein the tab has an emissivity greater than or equal to 0.90.

An eleventh aspect A11 includes the monitoring system of any of the first through tenth aspects, wherein the infrared detector comprises a long wave infrared camera.

A twelfth aspect A12 includes the monitoring system of any of the first through eleventh aspects, wherein the infrared detector periodically detects temperature data from the field of view at a predetermined interval and the temperature sensor periodically detects the tab temperature of the tab at the predetermined interval.

A thirteenth aspect A13 includes the monitoring system of any of the first through twelfth aspects, further comprising an ambient sensor communicatively coupled to the control unit, wherein the ambient sensor is configured to measure an ambient temperature adjacent to the field of view.

A fourteenth aspect A14 includes the monitoring system of any of the first through thirteenth aspects, wherein the computer readable and executable instructions, when executed by the processor, further cause the processor to calibrate the detected temperature of the subject and the detected temperature of the tab based on the ambient temperature.

A fifteenth aspect A15 includes method for monitoring a core temperature of a subject using a system comprising an infrared detector, a temperature sensor, and a tab, the method comprising: capturing thermal images of a target area with the infrared detector, the target area including the subject and the tab, wherein the thermal images comprise a plurality of pixels corresponding to at least a detected temperature of the subject and a detected temperature of the tab; measuring a reference temperature of the tab with the temperature sensor positioned on the tab; determining a difference between the detected temperature of the subject and the detected temperature of the tab from the thermal images; and computing the core temperature of the subject by adding the difference to the reference temperature of the tab.

A sixteenth aspect A16 includes the method of the fifteenth aspect, further comprising initiating an alert in response to the core temperature of the subject exceeding a predetermined threshold, wherein the alert comprises at least one of an audible message, a visual display, and a tactile feedback.

A seventeenth aspect A17 includes the method of any of the fifteenth through sixteenth aspects, further comprising calibrating the detected temperature of the subject and the detected temperature of the tab with an ambient temperature of the target area, wherein the ambient temperature is measured by an ambient sensor.

An eighteenth aspect A18 includes a monitoring system comprising: an infrared detector configured to capture thermal images of a target area; a tab positioned within the target area such that the infrared detector is configured to capture thermal images of the tab; a temperature sensor positioned on the tab and configured to measure a temperature of the tab; and an ambient sensor configured to measure an atmospheric temperature adjacent to the target area.

A nineteenth aspect A19 includes the monitoring system of the nineteenth aspect, further comprising a processor in communication with the infrared detector, the temperature sensor, and the ambient sensor, the processor configured to: analyze thermal data from the infrared detector corresponding to a subject within the target area and the tab to detect a temperature of the subject and the tab; analyze thermal data from the temperature sensor corresponding to the tab to detect a reference temperature of the tab; analyze thermal data from the ambient sensor to detect the atmospheric temperature; compute a corrected temperature of the subject and the tab by calibrating the detected temperatures of the subject and the tab with the atmospheric temperature; and compute a core temperature of the subject by adding the reference temperature of the tab to a difference between the corrected temperatures of the subject and the tab.

A twentieth aspect A20 includes the monitoring system of any of the eighteenth or nineteenth aspects, wherein the processor is configured to generate monitoring information relating to the core temperature of the subject, wherein the monitoring information comprises an alert generated in response to the processor determining the core temperature exceeds a predetermined temperature threshold.

Additional features of the monitoring system and methods for operating monitoring system described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
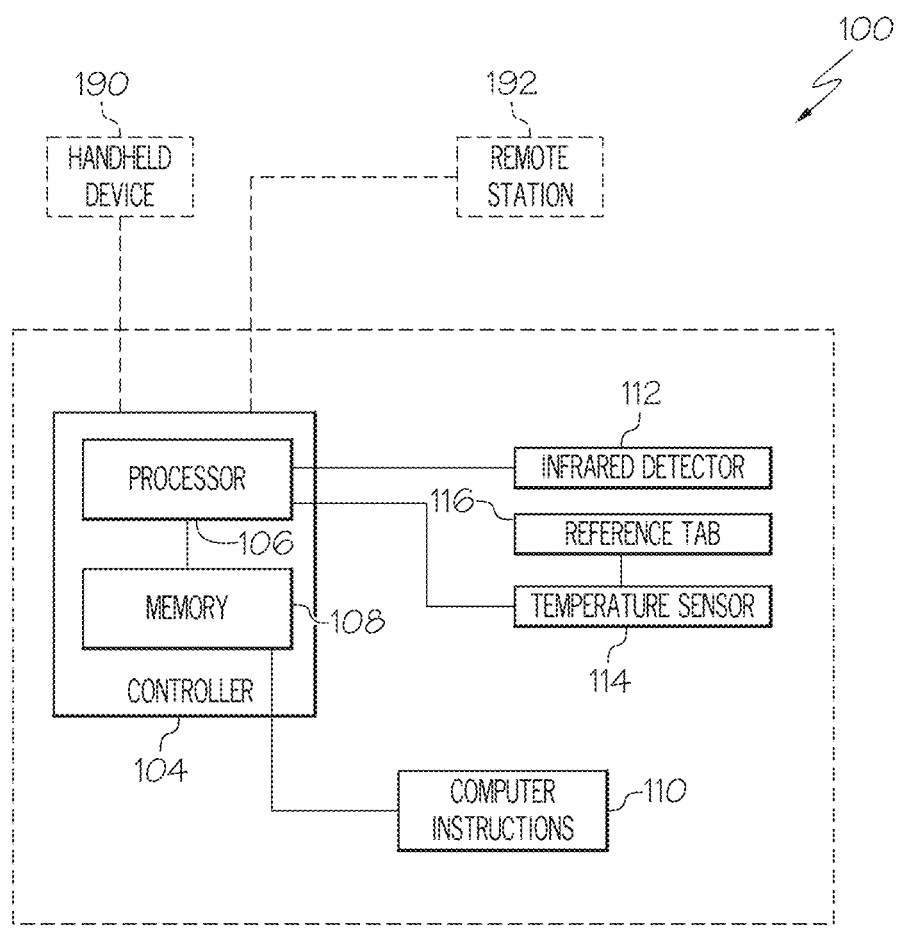
FIG. 1 schematically depicts a block diagram of a monitoring system according to one or more embodiments shown and described herein.

Reference will now be made in detail to embodiments of monitoring systems and methods of operating the same, examples of which are illustrated in the accompanying drawings. Whenever possible, the same reference numerals will be used throughout the drawings to refer to the same or like parts. Embodiments described herein are directed to a monitoring system that includes an infrared detector, a temperature sensor, and a tab. The infrared detector detects temperature data from a field of view and provides a signal indicative of characteristics of at least a detected temperature of a subject within the field of view. The tab is positioned within the field of view such that the infrared detector detects a temperature of the tab and emits a signal indicative of the detected temperature of the tab. The temperature sensor is secured to the tab to detect a temperature of the tab and provide a signal indicative of a reference temperature. A control unit is communicatively coupled to the infrared detector and the temperature sensor, and computes a net value between the detected temperature of the subject and the detected temperature of the tab, and calculates a core temperature of the subject by combining the net value with the reference temperature. Various embodiments of temperature monitoring systems for determining a change in temperature of a subject and method for using the same will be described herein with specific reference to the appended drawings.

As used herein, the phrase "communicatively coupled" is used to describe the interconnectivity of various components of the monitoring systems described herein and means that the components are directly or indirectly connected either through wires, optical fibers, or wirelessly such that electrical, optical, and/or electromagnetic signals may be exchanged between the components.

Referring initially to FIG. 1, a block diagram of a monitoring system 100 is schematically depicted. The monitoring system 100 generally comprises a controller 104 that may be communicatively coupled to at least one monitor. In some embodiments, the at least one monitor may comprise, for example and without limitation, a handheld device 190 and/or a remote station 192. The controller 104 comprises at least one processor 106 and at least one non-transitory memory module 108 that are communicatively coupled to one another. The non-transitory memory module 108 includes computer readable and executable instructions 110 that may be executed by the processor 106. Accordingly, it should be understood that the at least one processor 106 may be any device capable of executing the computer readable and executable instructions 110. For example, the processor 106 may be a controller, an integrated circuit, a microchip, a computer, or any other computing device. In the embodiment depicted in FIG. 1, the monitoring system 100 further includes an infrared detector 112, a temperature sensor 114, and a tab 116. The processor 106 of the controller 104 is communicatively coupled to the infrared detector 112 and temperature sensor 114.

Figure 2:
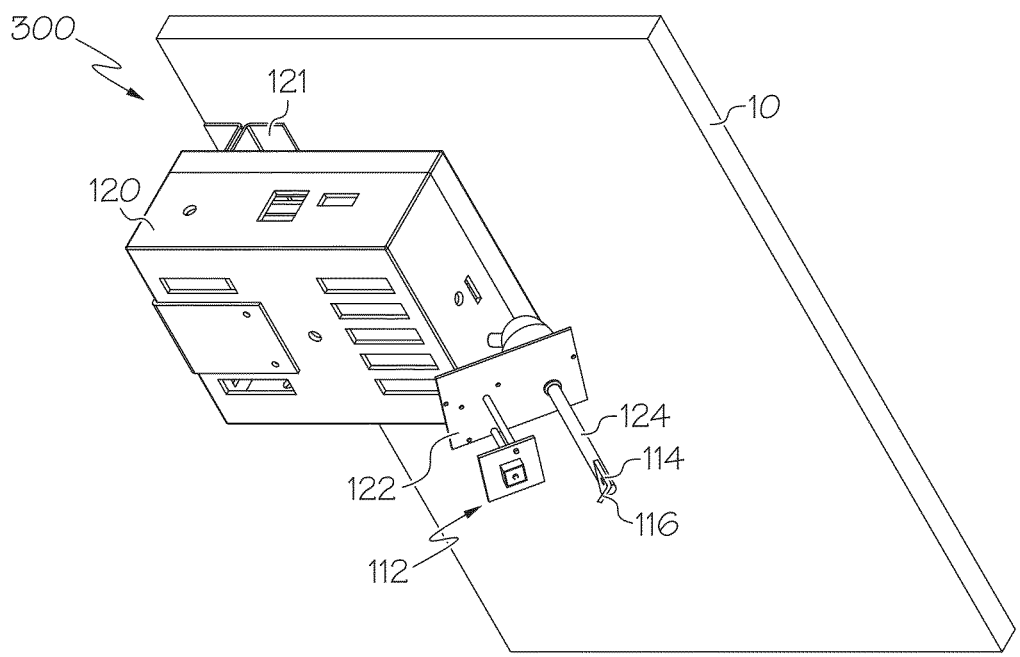
FIG. 2 depicts a perspective view of a monitoring system coupled to a ceiling panel, according to one or more embodiments shown and described herein.

Referring now to FIGS. 1 and 2, in the embodiments described herein the infrared detector 112 may be capable of detecting infrared radiation from a target area 15 and outputting a signal indicative of the temperature of the target area. Specifically, the infrared detector 112 comprises a field of view 14 that defines the target area 15 and the infrared detector 112 detects infrared radiation emitted from an object within the field of view 14 and the target area 15, such as a subject, and outputs a signal corresponding to the temperature of the infrared radiation emitted by the object. The controller 104 receives the signal generated by the infrared detector 112. In embodiments, the controller 104 may be configured and operable to determine if a subject positioned in the target area 15 has experienced a change in core temperature that exceeds a predetermined temperature threshold relative to a baseline core temperature of the subject, as will be described in greater detail below.

Additionally, by way of further example, the controller 104 may be configured and operable to determine a reference temperature for comparison and/or analysis when determining the core temperature of the subject. In particular, the controller 104 may utilize a reference temperature to adjust the temperature detected with the infrared detector 112. In some embodiments, the controller 104 may generate and transmit an alert to or through one or more of a handheld device 190 and remote station 192 when the determined core temperature of a subject 12 (FIG. 5) exceeds the predetermined temperature threshold. In other embodiments, the controller 104 may transmit the core temperature of the subject 12 to the remote station 192, and the remote station 192 thereby determines whether the core temperature of the subject 12 exceeds the predetermined temperature threshold. In that instance, the remote station 192 outputs an alert through the handheld device 190, the remote station 192, and/or both. As will be described in greater detail below, an alert may be in the form of an audible message, a visual display, or a tactile feedback.

In some embodiments, the infrared detector 112 is a thermal imaging camera utilizing uncooled microbolometer technology. The thermal imaging camera detects thermal radiation in the infrared portion of the electromagnetic spectrum from objects, such as a subject 12 (FIG. 5) and/or the like, located within the field of view 14 of the thermal imaging camera. The thermal imaging camera forms a thermal image based on the detected thermal radiation. Discrete portions of the thermal image correspond to discrete temperatures emitted by the objects within the field of view 14 of the thermal imaging camera. In embodiments, the thermal imaging camera is capable of determining a temperature of a region of the image (e.g., the face of a subject positioned in the field of view of the thermal imaging camera) by averaging the discrete temperatures of the thermal image within the region.

Figure 5:
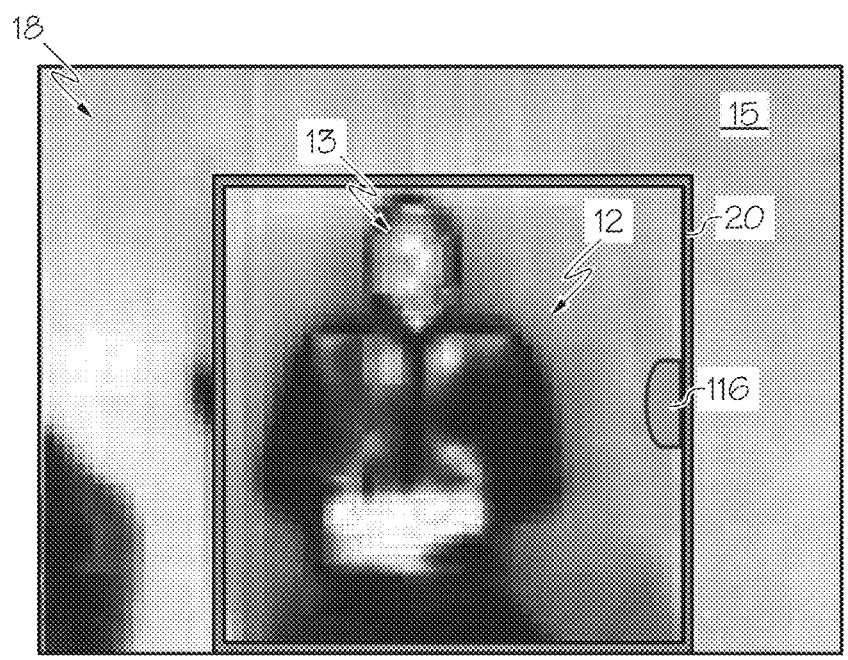
FIG. 5 is a thermal image formed by the infrared detector of the monitoring system of FIG. 1, according to one or more embodiments shown and described herein.

In embodiments, the infrared detector 112 may comprise a long-wave infrared thermal imaging camera that is configured to capture infrared radiation emitted from objects positioned within the field of view 14 of the infrared detector 112. In particular, the infrared detector 112 may be a camera that is sensitive to wavelengths of infrared radiation from about 8 micrometers to about 14 micrometers, such as those emitted by human bodies, for example a subject 12 (FIG. 5). That is, the infrared detector 112 comprises an array of sensors (not shown) that are formed of a material capable of detecting long-wave infrared radiation. For example, and without limitation, the infrared detector 112 may be a FLIR Lepton® LWIR Camera Module, manufactured by FLIR® Systems, Inc., Wilsonville, Oreg. In other embodiments, the infrared detector 112 may comprise an infrared temperature transducer and/or other like devices.

Still referring to FIGS. 1 and 2, in some embodiments the monitoring system 100 may comprise a housing 120 that contains the at least one processor 106 and the at least one non-transitory memory module 108 therein, among other internal components as will be described in greater detail below. For instance, the housing 120 may include a network/communication module to allow for communication between the controller 104 and various remote devices, such as, for example, the handheld device 190 and/or the remote station 192. In embodiments, the housing 120 of the monitoring system 100 may be mounted to a ceiling panel 10 of a room via a mounting apparatus 121 (such as a bracket or the like) such that the monitoring system 100 may be utilized to monitor a subject 12 (FIG. 5) located in the room as will be described further herein. For example, in embodiments, the monitoring system 100 may be mounted above a patient support apparatus (e.g., a bed or chair) to monitor a temperature of a face of a subject.

The monitoring system 100 further includes a base plate 122 coupled to the housing 120. Base plate 122 is sized and shaped to support the infrared detector 112, the temperature sensor 114, and the tab 116 thereon. The temperature sensor 114 and the tab 116 extend from the base plate 122 of the monitoring system 100 along an extension arm 124. The extension arm 124 is sized and shaped to support and couple the temperature sensor 114 and the tab 116 to the base plate 122, and in particular, to position the tab 116 within the field of view 14 of the infrared detector 112.

In the embodiments described herein, the temperature sensor 114 comprises a device configured to detect a temperature of an object and is positioned on the tab 116. For example, the temperature sensor 114 may be a TMP116

Temperature Sensor Chip manufactured by Texas Instruments®, Dallas, Tex. The temperature sensor is configured to have a high degree of temperature measurement accuracy, for example, within a range of approximately ±2° Celsius so as to accurately measure the temperature of the tab 116. As will be described in greater detail herein, the temperature sensor 114 is included in the monitoring system 100 to detect data relating to the tab 116, and in particular, to detect a temperature of the tab 116 that the temperature sensor 114 is positioned on. As will be described herein, the temperature of the tab 116 serves as a reference temperature used for computing an accurate core temperature of a subject.

In the embodiments described herein, the reference temperature is utilized to offset the signal noise intrinsic to thermal imaging devices utilizing uncooled microbolometer technology, such as the infrared detector 112, which may affect the accuracy of temperature measurements of the subject 12, as will be described in further detail herein.

In the embodiments described herein, the tab 116 has an emissivity greater than or equal to 0.90 to approximate the emissivity of a black body source. In some embodiments, the tab 116 may include an emissivity greater than or equal to 0.95. In embodiments, the tab 116 may be formed of a substrate material, such as glass fiber reinforced epoxy resin (e.g., printed circuit board ("PCB") material), coated and/or painted along an external surface of the tab 116 with a second material having the desired emissivity, such as black silicone paint, lampblack paint or the like. However, it should be understood that, in other embodiments, the tab 116 is formed from a material having the desired emissivity without the need for an additional coating or paint.

Figure 3:
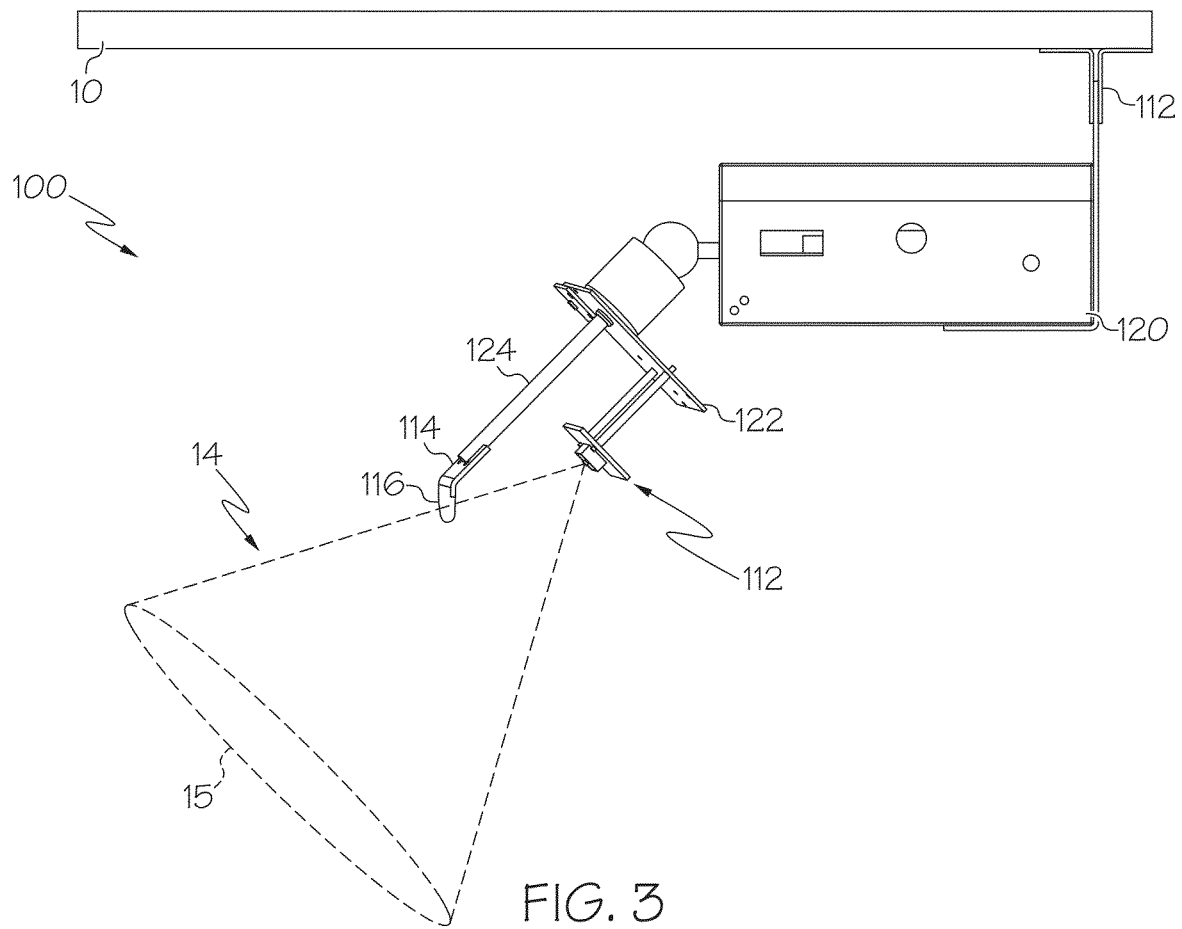
FIG. 3 depicts a side view of the monitoring system of FIG. 2 projecting a field of view comprising a target area from an infrared detector, according to one or more embodiments shown and described herein.

Referring now to FIGS. 2-3, the tab 116 extends from the extension arm 124 at a predetermined angle such that at least a portion of the tab 116 is positioned within the field of view 14 of the infrared detector 112. In embodiments, the temperature sensor 114 is securely coupled to the tab 116 along a portion of the tab 116 such that the temperature sensor 114 is external to (i.e. outside of) the field of view 14 of the infrared detector 112. However, it should be understood that in other embodiments all or a portion of the temperature sensor 114 may be positioned within the field of view 14 of the infrared detector 112 so long as at least a portion of the tab 116 is exposed and visible to the infrared detector 112 so that the infrared detector 112 can detect the temperature of the tab 116. Accordingly, it should be understood that the infrared detector 112 is capable of detecting a surface temperature of at least a portion of the tab 116 positioned within the field of view 14 of the infrared detector 112, in addition to detecting the surface temperatures of any other objects positioned within the field of view 14 of the infrared detector 112, including those within the target area 15 of the field of view 14.

Figure 4:
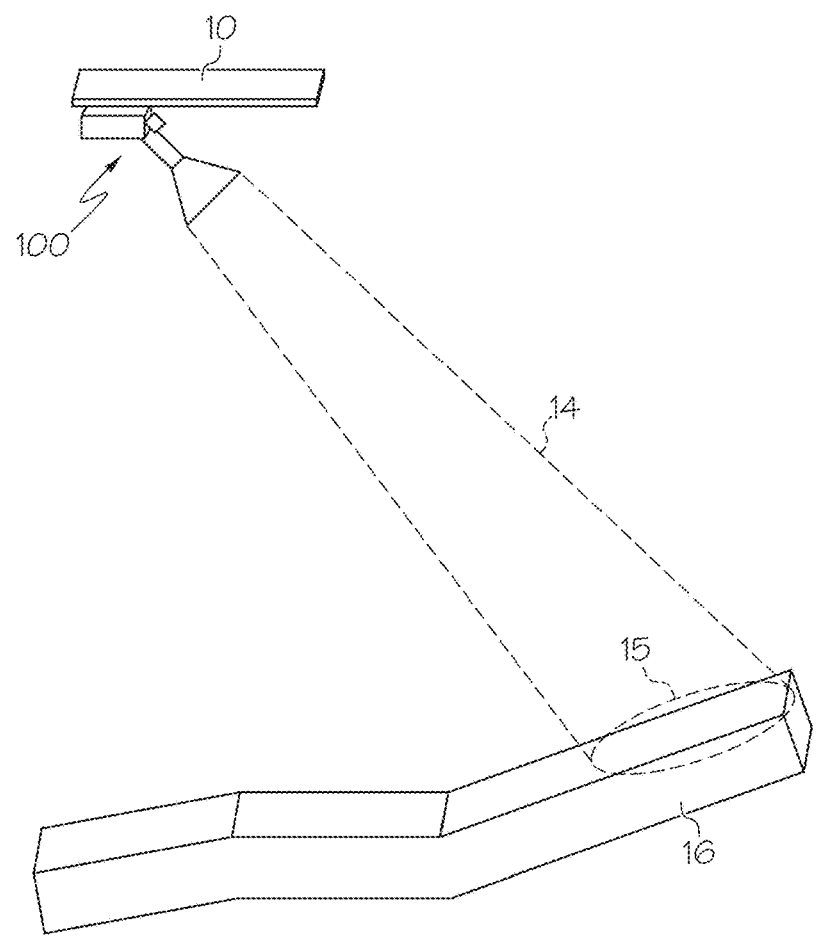
FIG. 4 depicts a side view of the monitoring system of FIG. 2 projecting the field of view toward a schematic depiction of a patient support such that the patient support is within the target area of the field of view, according to one or more embodiments shown and described herein.

For example, as seen in FIG. 4, the field of view 14 of the infrared detector 112 may be directed toward a patient support apparatus 16 (e.g., a bed and/or chair) such that a target area 15 of the field of view 14 is located on a surface of the patient support apparatus 16. In turn, any radiation emitted from an object positioned on the patient support apparatus 16 within the target area 15 is detected by the infrared detector 112 and evaluated by the controller 104. For example, with a subject 12 (FIG. 5) positioned on the patient support apparatus 16, the infrared detector 112 may detect heat (i.e., infrared radiation) radiating from the subject 12. In some embodiments, the field of view 14 and corresponding target area 15 of the infrared detector 112 may be repositioned, reoriented, enlarged, minimized and/or adjusted in accordance with desired preferences of an operator. For example, an orientation of the base plate 122 relative to the housing 120 may be adjusted to realign the infrared detector 112 and thereby cause an adjustment to the field of view 14 and/or the target area 15.

FIG. 5 depicts a sample thermal image 18 produced by the infrared detector 112. In some embodiments, the thermal image 18 may include a display frame 20 that may be determined and applied to the thermal image by the controller 104 of the monitoring system 100. The display frame 20 provides a boundary line that corresponds to an area within the target area 15 of the infrared detector 112. The display frame 20 is used by the controller 104 to define an area of interest of the thermal image 18 for analysis by the processor 106. The display frame 20 may be established and/or adjusted by the controller 104 based on the image received by the controller 104 from the infrared detector 112 using an object recognition algorithm that detects the location of the subject 12 within the thermal image 18. In particular, the display frame 20 defines a subset of data in the thermal image 18 that is determined by the object recognition algorithm to be relevant to the processor 106 for the purposes of computing a subject's temperature. Accordingly, the processor 106 may ignore any data detected by the infrared detector 112 that is positioned outside the display frame 20.

For example, the display frame 20 of the present example includes at least a facial region 13 of the subject 12 and a portion of the tab 116 positioned within the display frame 20 of the target area 15. While FIG. 4 depicts a visible display frame 20, it should be understood that the display flame 20 need not be visible on the image, such as when the controller 104 uses an object recognition algorithm to identify the area of interest without visibly manipulating the image. Further, while FIG. 4 depicts a display frame 20, it should be understood that in some embodiments the monitoring system 100 may not include the display frame 20 such that all objects detected by the infrared detector 112 within the entire target area 15 are included in the data processed by the controller 104 of the monitoring system 100.

It should be understood that the thermal image 18 shown in FIG. 4 is an image of the subject 12 at a single point in time and depicts only the image data detected by the infrared detector 112 from the target area 15 related to that particular point in time. The monitoring system 100 may utilize a single thermal image 18 for processing and analysis, as will be described in further detail below, or the controller 104 may evaluate more than one thermal image 18 collected by the infrared detector 112 when evaluating the temperature characteristics of the subject 12 and the tab 116. For example, the monitoring system 100 may be programmed to retrieve multiple thermal images 18 from the infrared detector 112 for analysis over a predetermined period of time. As an illustrative example, the monitoring system 100 may monitor and evaluate two thermal images 18 of the target area 15 when determining a core temperature of the subject 12. Alternatively, in other embodiments, the monitoring system 100 may be programmed to periodically detect one or more thermal images 18 at a predetermined time interval (e.g., about 10 minutes to about 15 minutes) to continuously monitor the core temperature of the subject 12 over an extended duration.

The handheld device 190 and the remote station 192 are remote devices that are communicatively coupled to one another and to the controller 104. The remote station 192 may include a processor and a non-transitory memory module that are communicatively coupled to one another, wherein the non-transitory memory module of the remote station 192 includes computer readable and executable instructions that may be executed by the processor of the remote station 192. It embodiments, the initialization of the monitoring system 100 may be achieved via the at least one handheld device 190 and/or the at least one remote station 192. Further, in some embodiments the remote station 192 may be configured to receive the temperature data described above from the controller 104 after the infrared detector 112 and the temperature sensor 114 detect the temperature characteristics of the subject 12 and the tab 116, respectively. Once received at the remote station 192, the processor of the remote station 192 is operable to determine whether the core temperature of the subject 12, as computed by the processor 106 with the data retrieved by the infrared detector 112 and the temperature sensor 114, exceeds a predetermined temperature threshold.

In this instance, the remote station 192 may store a baseline temperature of a subject within the non-transitory memory module of the remote station 192 for purposes of comparing with the data received from the controller 104 to determine whether the predetermined temperature threshold is exceeded. The predetermined temperature threshold is programmed and stored within the non-transitory memory module of the remote station 192 and, dependent on a preference of an operator of the monitoring system 100, the predetermined temperature threshold may be input into the remote station 192. As merely an illustrative example, the predetermined temperature threshold may range from about ±1.0° Celsius to about ±0.20° Celsius, and in particular, about ±0.5° Celsius.

In the instance where the core temperature of the subject as measured by the controller 104 exceeds the baseline temperature programmed in the remote station 192 by the predetermined temperature threshold, the processor of the remote station 192 is operable to transmit a signal initiating an alert that the temperature data identified by the controller 104 exceeds the threshold. In embodiments, the alert may be communicated to an operator of the monitoring system 100 at the remote station 192, while in other embodiments the signal may be communicated to the handheld device 190 such that the alert is outputted via the handheld device 190. It should be understood that in some embodiments the determination of whether the temperature data identified by the infrared detector 112 and temperature sensor 114 exceeds the predetermined temperature threshold may occur at the processor 106 such that the controller 104 performs the analysis described above and thereby transmits a signal to the handheld device 190 and/or the remote station 192 to generate the alert.

Figure 6:
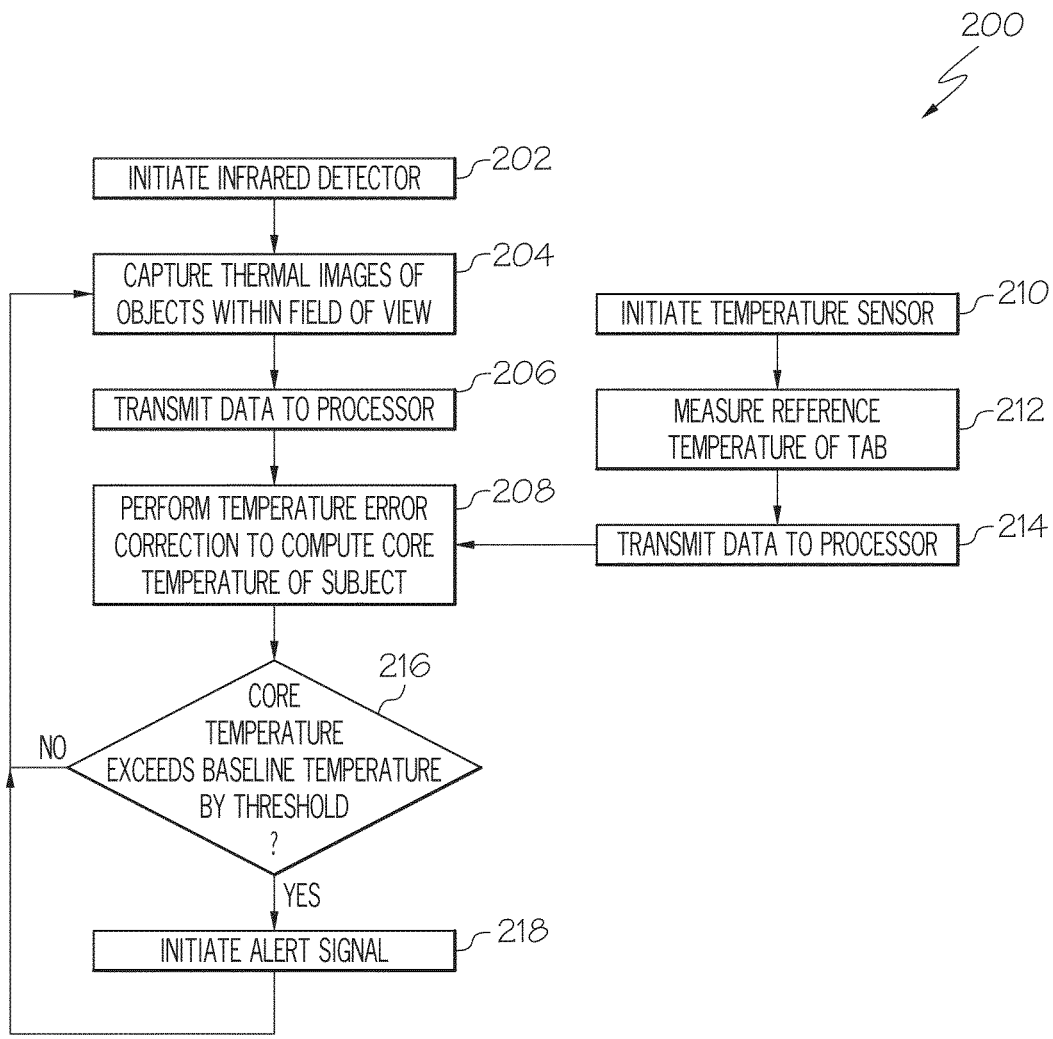
FIG. 6 is a flow chart of a method for monitoring a temperature of a subject positioned within the target area of the monitoring system of FIG. 1, according to one or more embodiments shown and described herein.

FIG. 6 is a flowchart of one method 200 of using the monitoring system 100 described above. It should be understood that method 200 is merely illustrative and that the monitoring system 100 may be utilized in other various methods. In particular, a baseline temperature of a subject 12 is determined for use by the monitoring system 100 at initialization of the monitoring system 100. The baseline temperature is an initial core temperature of the subject 12 that is stored in the non-transitory memory module 108. In some embodiments, the baseline temperature may be determined by the monitoring system 100 upon start-up, such as in response to initialization of the monitoring system 100 by an operator through a monitor such as the handheld device 190 and/or the remote station 192, and stored in the non-transitory memory module 108. In some other embodiments, the baseline temperature is input into the monitoring system 100 by an operator and thereby stored in the non-transitory memory module 108. In these embodiments, the baseline temperature of the subject may be obtained by conventional methods for measuring body temperature. For example, a baseline temperature may be measured utilizing a temperature probe or thermometer (e.g., by inserting the probe or thermometer into the mouth, ear, armpit, etc.).

In other embodiments, the monitoring system 100 may retrieve the baseline temperature of the subject 12 by performing the steps described herein and shown in FIG. 6. For example, an operator of the monitoring system 100 may detect the baseline temperature of the subject 12 by initializing the monitoring system 100 via the at least one handheld device 190 and/or the at least one remote station 192 to perform the steps noted below to retrieve an initial, baseline temperature.

The baseline temperature of the subject 12 is utilized by the monitoring system 100 in conjunction with core temperatures of the subject 12 subsequently measured with the monitoring system 100 to determine whether a change in the temperature of the subject has occurred and, if so, if the change in the temperature of the subject exceeds a predetermined temperature threshold during the duration that the subject 12 is present within the room where the monitoring system 100 is installed.

Referring to FIGS. 1-6, in a first step 202, the infrared detector 112 of the monitoring system 100 is initiated such that any objects positioned within the field of view 14 and target area 15 are detected by the infrared detector 112. The infrared detector 112 captures thermal image(s) of any objects within the field of view 14 of the target area 15 of the infrared detector 112, such as the subject 12 and the tab 116, at step 204. In particular, the thermal image(s) detected by the infrared detector 112 include a plurality of frame pixels. The individual frame pixels of the thermal image correspond to individual sensors in the array of sensors of the infrared detector 112. The array of sensors detect thermal radiation from discrete areas within the field of view 14 and the illumination of each pixel relates to the amount of heat detected by the corresponding sensor. Accordingly, frame pixels of the facial region 13 of the subject 12 and of the tab 116 indicate a respective temperature detected from the corresponding area of the thermal image 18.

The thermal image of the subject 12 and the tab 116 are transmitted from the infrared detector 112 to the processor 106 at step 206. In particular, a signal indicative of the temperature(s) of the facial region 13 of the subject 12 is transmitted to the processor 106, and similarly, a signal indicative of the temperature of the tab 116 is transmitted to the processor 106. The processor 106 determines the temperature data from the thermal image 18. In particular, a temperature derived from a plurality of frame pixels representing the facial region 13 of the subject 12 is determined, and a temperature derived from a plurality of frame pixels representing the portion of the tab 116 positioned within the field of view 14 is determined. With the temperature data received at the processor 106, the computer readable and executable instructions 110 stored within the non-transitory memory module 108 causes the processor 106 to perform a temperature error correction to compute a core temperature of the subject 12 positioned within the target area 15 of the infrared detector 112.

In particular, at step 208, the computer readable and executable instructions 110 cause the processor 106 to add the temperature(s) detected by the array of sensors corresponding to an area representing the facial region 13 of the subject 12 to calculate an average temperature of the subject 12 (i.e., a detected temperature of the facial region 13, $T_{Face}$) by dividing the aggregated temperature by the number of frame pixels corresponding to the facial region 13. Further, the computer readable and executable instructions 110 causes the processor 106 to add the temperature(s) detected by the array of sensors for an area corresponding to the portion of the tab 116 received within the target area 15, to calculate an average temperature of the tab 116 (i.e., a detected temperature of the tab 116, $T_{Tab}$) by dividing the aggregated temperature by the number of frame pixels corresponding to the tab 116.

Still referring to step 208, the processor 106 computes a difference between the detected temperature of the facial region 13 and the detected temperature of the tab 116, as shown in Equation (1) below. In particular, the processor 106 subtracts the detected temperature of the facial region 13 ($T_{Face}$) from the detected temperature of the tab 116 ($T_{Tab}$) to arrive at a net temperature value ($T_A$).

$$(T_{66}) = (T_{Face} - T_{Tab}) \quad \text{Equation (1)}$$

At step 210, the temperature sensor 114 is initiated to detect a reference temperature of the tab 116. In particular, at step 212, the temperature sensor 114 measures the temperature of the tab 116 ($T_{Ref}$) via the temperature sensor positioned on the tab 116. This reference temperature data is transmitted from the temperature sensor 114 to the processor 106 at step 214. In particular, a signal indicative of the reference temperature of the tab 116 ($T_{Ref}$) is transmitted to the processor 106. In this instance, referring back to step 208, the computer readable and executable instructions 110 stored in the at least one non-transitory memory module 108 cause the processor 106 to correct any temperature error from the detected temperature of the facial region 13 ($T_{Face}$) and the detected temperature of the tab 116 ($T_A$), as measured by the infrared detector 112, by adding the net temperature ($T_A$) to the reference temperature of the tab 116 ($T_{Ref}$), as measured by the temperature sensor 114 positioned on the tab 116, as indicated in Equation (2) below. In particular, the net temperature value (i.e., the difference between $T_{face}$ and $T_{Tab}$, $T_A$) is combined (i.e., added) with the reference temperature of the tab 116 ($T_{Ref}$) to calculate a core temperature of the facial region 13 of the subject 12 ($T_{core}$).

$$T_{core} = T_A + T_{Ref} \quad \text{Equation (2)}$$

As noted above, it should be understood that the monitoring system 100 may retrieve the baseline temperature of the subject 12 by performing the steps described above and by utilizing Equations (1) and (2). An operator of the monitoring system 100 may detect the baseline temperature of the subject 12 by initializing the monitoring system 100 via the at least one handheld device 190 and/or the at least one remote station 192 to perform the steps noted above to retrieve the initial, baseline temperature.

At step 216, the core temperature of the subject 12 ($T_{Core}$) is compared to the baseline temperature of the subject 12. In this instance, an inquiry is initiated to determine whether the core temperature ($T_{Core}$) of the facial region 13 of the subject 12 differs from the baseline temperature of the subject 12 (e.g., either greater than or less than the baseline temperature) by a predetermined temperature threshold. In particular, the predetermined temperature threshold is programmed in the computer readable and executable instructions 110 and/or stored in the non-transitory memory module 108 and corresponds to a temperature variance that signifies meaningful change in the temperature of the subject 12 which should be further addressed.

It should be understood that in some embodiments the predetermined temperature threshold may be preprogrammed in the computer readable and executable instructions 110 and/or stored in the at least one non-transitory memory module 108, while in other embodiments an operator of the monitoring system 100 may input a desired temperature threshold for use by the monitoring system 100. As described above, it should further be understood that the predetermined temperature threshold may be preprogrammed and/or input into a non-transitory memory module of the remote station 192 and/or the handheld device 190 such that the remote station 192 and/or the handheld device 190 performs the determination of whether the core temperature ($T_{Core}$) exceeds the baseline temperature by the predetermined temperature threshold.

At step 218, an affirmative response to the inquiry at step 216 provides for the initiation of monitoring information in the form of a report and/or an alert signal that is generated by the processor 106. The report and/or alert signal may be transmitted to an operator via a monitor, for example, the at least one handheld device 190 and/or the at least one remote station 192 described above, to inform an operator of the monitoring system 100 of the subject's core temperature, as detected by the monitoring system 100, and/or to alert an operator of a change in the subject's condition based on the core temperature ($T_{Core}$) relative to the baseline temperature. In particular, the computer readable and executable instructions 110 may be programmed to include a predetermined temperature threshold. In other embodiments, the non-transitory memory module 108 may include the predetermined temperature threshold stored therein. In this instance, the monitoring system 100 may be configured to initiate an alert when the core temperature ($T_{Core}$) varies (i.e., is greater than or less than) from the baseline temperature by more than the predetermined temperature threshold. It should be understood that in embodiments the predetermined temperature threshold is less than the error range of conventional infrared cameras (e.g., ±4° Celsius). For example, in some embodiments the predetermined temperature threshold may equal ±1° Celsius, and in other embodiments the threshold may equal ±0.5° Celsius.

For example, the subject may acquire a fever which is thereby detected by the monitoring system 100 by the deviation in core temperature ($T_{Core}$) relative to the baseline temperature that was measured prior to the occurrence of the fever. Accordingly, the alert is indicative of characteristics of the subject 12, and in particular, a change in core temperature of the subject 12. The alert may comprise an audible message for an operator to hear, a visual message for an operator to view, or a tactile feedback for an operator to perceive at the handheld device 190 and/or remote station 192. In some embodiments, the controller 104 may be positioned within the housing 120 such that the computer readable and executable instructions 110 may cause the processor 106 to transmit a signal to the monitor to initiate an alert. Once the alert signal has been transmitted, the method returns to step 204 and the method is repeated from step 204 at a predetermined interval, as described below.

Alternatively, in the event the inquiry at step 216 results in a determination that the core temperature of the subject 12 ($T_{Core}$) does not exceed the predetermined temperature threshold, the monitoring system 100 may return to step 204 and the method is repeated at a predetermined interval. In particular, the predetermined interval may be programmed in the computer readable and executable instructions 110 of the at least one non-transitory memory module 108 and corresponds to a periodic schedule for performing the method 200 with the monitoring system 100. It should be understood that in some embodiments the predetermined interval may be preprogrammed in the computer readable and executable instructions 110, while in other embodiments an operator of the monitoring system 100 may input a desired time interval for use by the monitoring system 100. By way of example only, the time internal may be programmed to about 10 minutes to about 15 minutes. In some embodiments, the method 200 of the monitoring system 100 may cease operation in response to the determination at step 216 that the core temperature of the subject 12 does not exceed the predetermined temperature threshold.

As described in greater detail above, it should be understood that the monitoring system 100 may be configured such that the determination of whether the core temperature of the subject 12 ($T_{core}$) exceeds the baseline temperature of the subject 12 by the predetermined temperature threshold occurs at the remote station 192 and/or the handheld device 190. In this instance, a non-transitory memory module of the remote station 192 stores the predetermined temperature threshold and the predetermined interval data and a processor of the remote station 192 computes the comparative analysis between the core temperature of the subject 12 ($T_{core}$) and the baseline temperature as described above.

Figure 7:
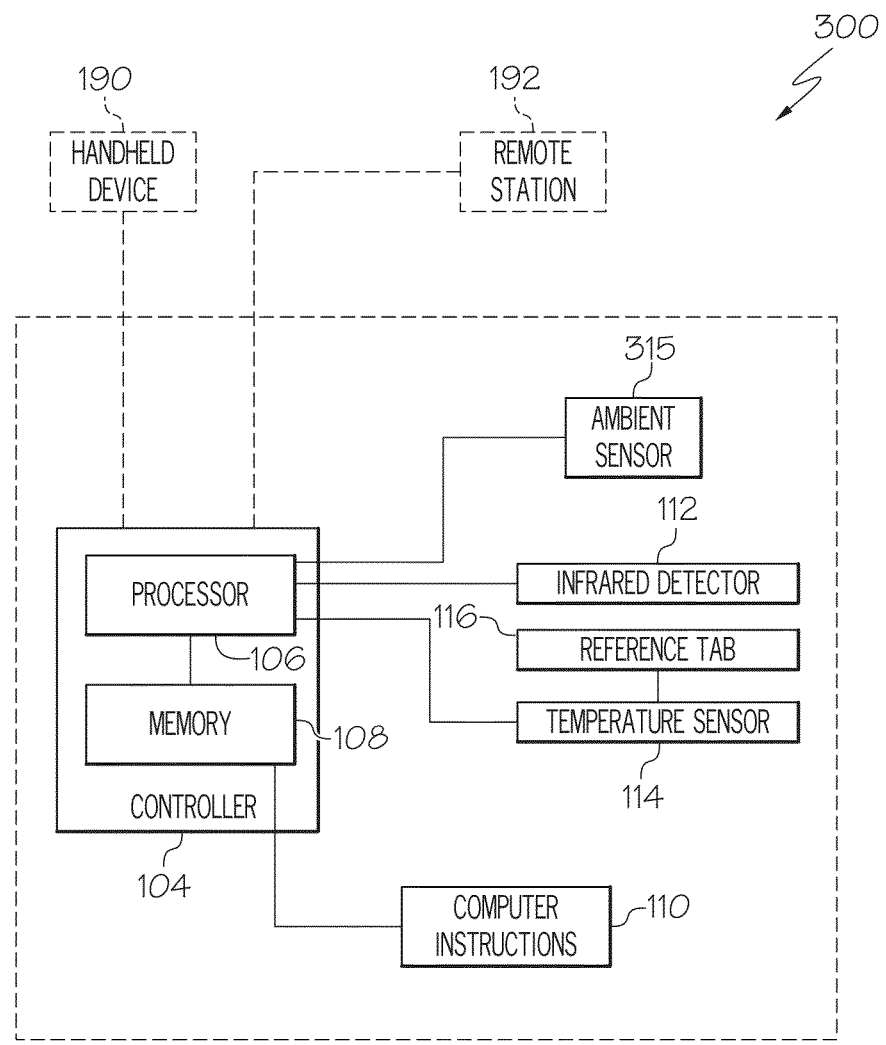
FIG. 7 schematically depicts a block diagram of an alternative monitoring system comprising a third detector for detecting an ambient temperature, according to one or more embodiments shown and described herein.

Referring now to FIG. 7, another monitoring system 300 is diagrammatically depicted. It should be understood that except as otherwise described below, the monitoring system 300 is substantially similar to and may have the same configuration and operation as the monitoring system 100. As such, the same reference numerals are used to identify the same components of the system. In this embodiment, the monitoring system 300 is different than the monitoring system 100 in that the monitoring system 300 further includes an ambient detector sensor communicatively coupled to the controller 104.

The ambient sensor 315 is capable of detecting the temperature of the ambient environment and outputting a signal indicative of the detected temperature to the controller 104. In some embodiments, the ambient sensor 315 comprises a temperature sensor configured to measure an ambient temperature of the room that the monitoring system 100 is located in. For example, the ambient sensor 315 may be a TMP116 Temperature Sensor Chip manufactured by Texas Instruments®, Dallas, Tex.

Figure 8:
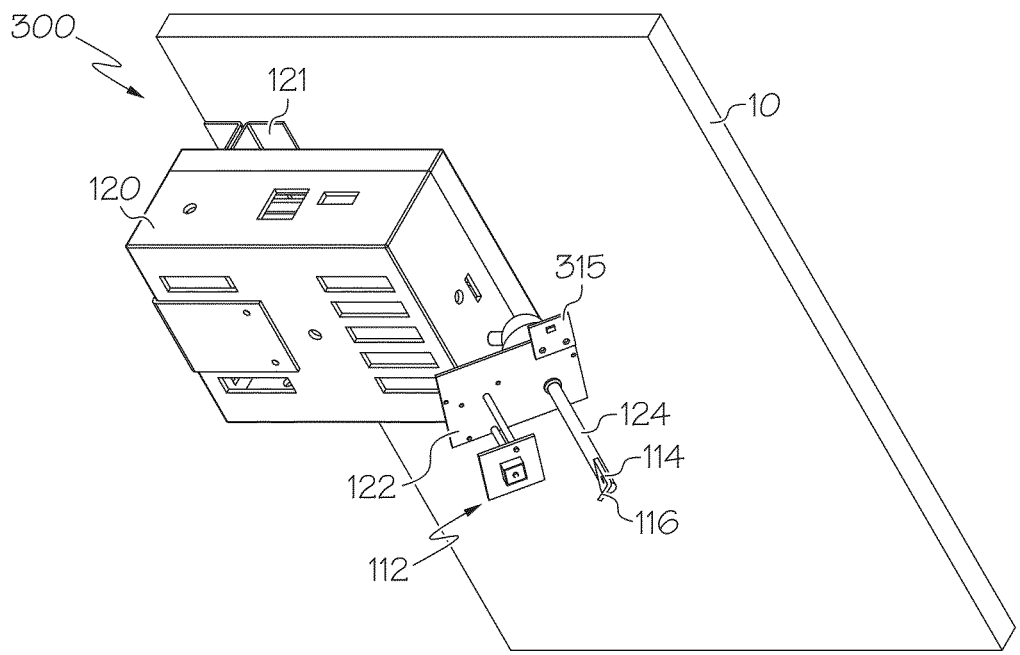
FIG. 8 depicts a perspective view of the monitoring system of FIG. 7 coupled to a ceiling panel, according to one or more embodiments shown and described herein.
Figure 9:
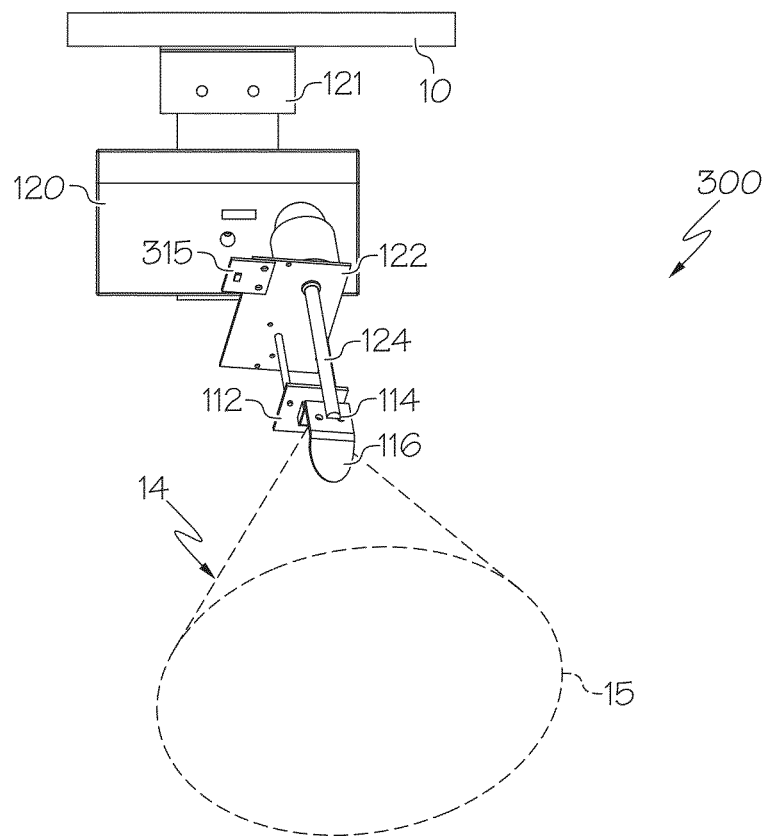
FIG. 9 depicts a perspective view of the monitoring system of FIG. 8 including the third detector, according to one or more embodiments shown and described herein.

Referring now to FIGS. 8 and 9, the ambient sensor 315 is secured to the housing 120 independent of the tab 116 and the subject 12. The temperature data detected by the ambient sensor 315 is transmitted to the processor 106 as a signal indicative of the ambient temperature to assist with calibrating the temperature measurements made with the infrared detector 112. Calibrating the detected temperature of the subject 12 ($T_{Face}$) and the detected temperature of the tab 116 ($T_A$), with use of the ambient sensor 315, prior to computing the core temperature ($T_{Core}$) of the subject 12 may improve the overall accuracy of the core temperature ($T_{Core}$) of the subject 12 computed by the monitoring system 300.

As discussed above, the infrared detector 112 comprises a long-wave infrared thermal imaging camera that is configured to capture infrared radiation emitted from objects positioned within the field of view 14 of the infrared detector 112. It should be understood that prior to utilizing the monitoring system 300 to determine and monitor a core temperature of a subject, the infrared detector 112 of the monitoring system 300 requires calibration, and in particular, various calibration parameters of the infrared detector 112 are determined to ensure accuracy of temperature data retrieved by the infrared detector 112. For instance, long-wave infrared thermal imaging cameras may include calibration parameters such as camera responsivity (R), camera offset (O), and camera curve correction parameters (F) and (B). In the present example, it should be understood that the curve correction parameters "F" and "B" are fixed and maintained at standard specifications of the thermal imaging camera (i.e., infrared detector 112) utilized in the monitoring system 300. By way of example only, the curve correction parameter (F) is set to 1.0 and the curve correction parameter (B) is set to 1428. It should be understood that in other embodiments the curve correction parameters may vary dependent on the type of thermal imaging camera utilized in the monitoring system 300, the manufacturer of the thermal imaging camera, the setting in which the monitoring system 300 is utilized, and the like.

Camera responsivity (R) and camera offset (O) parameters of the infrared detector 112 are determined and calibrated by utilizing a reference point having a known temperature, such as, for example, the tab 116. In this instance, the temperature of the tab 116 is known due to the inclusion of the temperature sensor 114 positioned on the tab 116. As discussed in detail above, the temperature sensor 114 is configured and operable to measure a temperature of the tab 116 with relatively high accuracy (e.g., ±0.2° Celsius). With the reference temperature of the tab 116 known by the temperature sensor 114, the infrared detector 112 may utilize the tab 116 to determine a detected temperature of the tab 116, which is thereby compared to the reference temperature. Accordingly, the camera responsivity (R) and camera offset (O) of the infrared detector 112 may be selectively adjusted to calibrate the infrared detector 112 until the detected temperature of the tab 116, as determined by the infrared detector 112, is substantially similar (e.g., within ±0.5° Celsius) to the reference temperature of the tab 116 as determined by the temperature sensor 114.

In particular, with the reference temperature ($T_{Reference}$) of the tab 116 known and the calibration parameters (B), (F), (R) and (O) of the infrared detector 112 set, a detected temperature $W(T_{Detected})$ of the tab 116, as determined by the infrared detector 112, may be compared to the reference temperature ($T_{Reference}$) using Equation (3) below.

$$T_{Reference} = \frac{B}{\ln\left(\frac{R}{W(T_{Detected}) - O} + F\right)} \qquad \text{Equation (3)}$$

The camera responsivity (R) and camera offset (O) parameters of the infrared detector 112 may be adjusted by an operator until the detected temperature of the tab 116 as determined by the infrared detector 112 is equal to the reference temperature ($T_{Reference}$) of the tab 116 as determined by the temperature sensor 114, thereby calibrating the infrared detector 112 for use by the monitoring system 300. It should be understood that the infrared detector 112 is calibrated once at the initial installation of the monitoring system 300 such that the infrared detector 112 is not required to be subsequently calibrated during use of the monitoring system 300.

With the infrared detector 112 calibrated, the monitoring system 300 is operable for use in monitoring a subject 12 and the ambient sensor 315 is operable to calibrate the detected temperature of the subject 12 ($T_{Face}$) and the detected temperature of the tab 116 ($T_A$) to improve the overall accuracy of the core temperature ($T_{core}$) of the subject 12 computed by the monitoring system 300. In particular, the monitoring system 300 is configured to utilize temperature data determined by the ambient sensor 315 to perform error correction calculations prior to computing the core temperature ($T_{Core}$) of the subject 12.

In one example of this error correction calculation, a scene temperature $T_{Scene}$ (in Kelvin) is calculated for the facial region 13 of the subject 12 ($T_{Face}$) and the tab 116 ($T_{Tab}$) using Equations (4) and (5) below (i.e., the "scene" may be either the "face" or the "tab", hence $T_{Scene}$ may be either $T_{Face}$ or $T_{Tab}$ and the like). In particular, a corrected thermal flux $W(T_{Scene})$ is calculated for the plurality of pixels within the target area 15 defining the "scene" of the facial region 13, via Equation (4) below. The atmospheric temperature ($T_{Atm}$) measured by the ambient sensor 315 (in Kelvin) is factored into the exponential function along with the heat flux (S) of the facial region 13, as measured by the infrared detector 112, to arrive at the corrected thermal flux for the facial region 13 (i.e., $W(T_{Face})$). As described above, the heat flux (S) (in counts) is the temperature absorbed by each sensor in the array of sensors of the infrared detector 112 such that the computer readable and executable instructions 110 cause the processor 106 to add the temperature(s) detected by the array of sensors corresponding to the area representing the facial region 13 of the subject 12 to calculate an average temperature of the subject 12 by dividing the aggregated temperature by the number of frame pixels corresponding to the facial region 13 to arrive at the heat flux (S). Further, the function for calculating the corrected thermal flux $W(T_{Scene})$ includes a transmittance coefficient ($\tau_{atm}$) of the atmosphere between the scene and the infrared detector 112, and the emissivity (E) of the scene.

$$W(T_{Scene}) = \frac{S}{(\tau_{Atm} * E)} - \frac{(1-E)}{E} * W(T_{Atm}) - \frac{(1-T_{Atm})}{(T_{Atm} * E)} * W(T_{Atm}) \qquad \text{Equation (4)}$$

By factoring in the atmospheric temperature ($T_{Atm}$) into the calculation of the thermal flux measurement of the facial region 13, as measured by the ambient sensor 315, a corrected thermal flux $W(T_{Face})$ is computed for the facial region 13 of the subject 12. With the corrected thermal flux computed for the facial region 13, a calibrated scene temperature ($T_{Scene}$) of the facial region 13 (i.e., $T_{Face}$) may be computed, using Equation (5) below. In particular, the calibration parameters of the infrared detector 112 (e.g., a thermal imaging camera), as discussed above, are factored into the corrected thermal flux $W(T_{Scene})$ of the facial region 13 to determine the calibrated scene temperature ($T_{Scene}$) of the facial region 13 (i.e., $T_{Face}$).

$$T_{Scene} = \frac{B}{\ln\left(\frac{R}{W(T_{Scene})-O} + F\right)} \qquad \text{Equation (5)}$$

With the calibrated scene temperature of the facial region 13 ($T_{Face}$) computed, a similar error correction calculation may be calculated for the portion of the tab 116 within the target area 15, using Equations (4) and (5) as similarly described above. In this instance, a corrected thermal flux $W(T_{Tab})$ is calculated for the plurality of pixels within the target area 15 defining the "scene" of the tab 116 via Equation (4), and the scene temperature ($T_{Tab}$) of the tab 116 may be computed using Equation (5) above. With the scene temperatures ($T_{Face}$ and $T_{Tab}$) representing calibrated surface temperatures of the facial region 13 and the tab 116, by having factored in the ambient temperature ($T_{Atm}$) as measured by the ambient sensor 315 and the calibration parameters of the infrared detector 112, a core temperature of the subject 12 ($T_{Core}$) may be computed with relatively greater accuracy using Equation (6) below. In particular, a core temperature of the subject 12 ($T_{Core}$) is computed by adding the net value between the scene temperatures ($T_{Face}$, $T_{Tab}$) with the reference temperature of the tab 116 ($T_{Ref}$), as determined by the temperature sensor 114.

$$T_{Core} = (T_{Face} - T_{Tab}) + (T_{Ref}) \qquad \text{Equation (6)}$$

Figure 10:
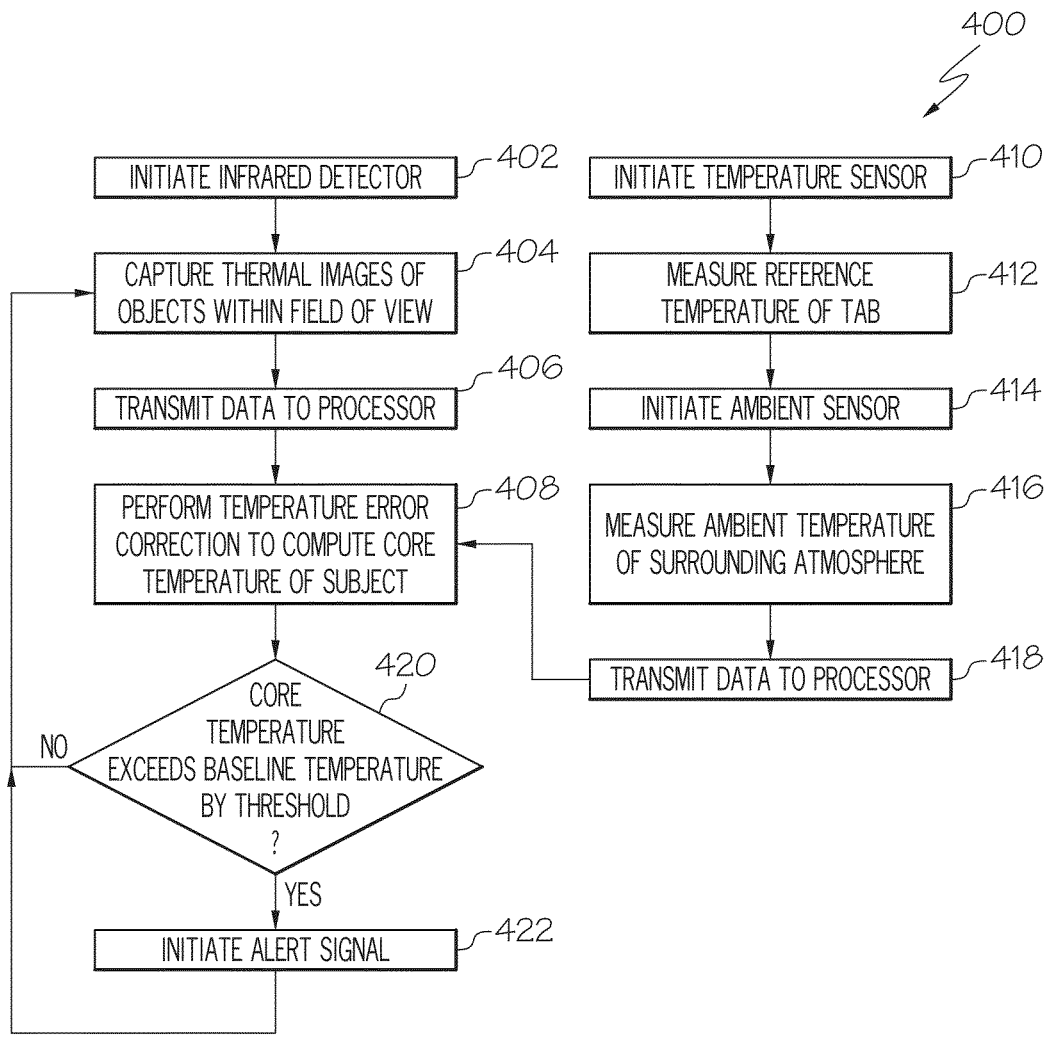
FIG. 10 is a flow chart of a method for monitoring a temperature of a subject positioned within the target area of the monitoring system of FIG. 7, according to one or more embodiments shown and described herein.

FIG. 10 is a flow chart of one method 400 of using the monitoring system 300 described above. It should be understood that method 400 is merely illustrative and that the monitoring system 300 may be utilized in other various methods. It should be further understood that the monitoring system 300 of the present example is configured to compute a core temperature ($T_{Core}$) of a subject 12 in a substantially similar manner to the example method 200 described above and shown in FIG. 6, except for the differences explicitly described below. For instance, a baseline temperature of a subject 12 may be determined in a substantially similar process as that described above, i.e., via use of a temperature probe, a thermometer, and/or the monitoring system 300.

Referring now to FIGS. 5 and 7-10, in a first step 402, the infrared detector 112 of the monitoring system 300 is initiated such that any objects positioned within the field of view 14 of the target area 15 of the infrared detector 112 are detected. In particular, the infrared detector 112 captures a thermal image(s) of any objects within the field of view 14 emitting a temperature, such as the subject 12 and the tab 116, at step 404. An array of sensors of the infrared detector 112 directed at a facial region 13 of the subject 12 and at the tab 116 corresponds to the individual frame of pixels of the thermal image. The individual frame pixels of the thermal image correspond to individual sensors in the array of sensors of the infrared detector 112. The array of sensors detect thermal radiation from discrete areas within the field of view 14 and the degree of illumination of each pixel relates to the amount of heat detected by the corresponding sensor.

The thermal image of the subject 12 and the tab 116 are transmitted from the infrared detector 112 to the processor 106 at step 406. In particular, signals indicative of the temperature of the facial region 13 of the subject 12 and the tab 116 are transmitted to the processor 106. The processor 106 calculates the core temperature ($T_{Core}$) from the temperature data detected by the infrared detector 112 of the subject 12 and the tab 116 in accordance with the Equations (4), (5) and (6) described above. In particular, a detected temperature of the subject 12, derived from a plurality of pixels representing the facial region 13 of the subject 12, and a detected temperature of the tab 116, derived form a plurality of pixels representing the tab 116, are determined by the processor 106. At step 410, the temperature sensor 114 is initiated to detect a reference temperature of the tab 116, and in particular, at step 412, the temperature sensor 114 measures a temperature of the tab 116. The ambient sensor 315 is similarly initiated at step 414 to detect an ambient temperature of the room that the monitoring system 300 is located in, and in particular, at step 416, the ambient sensor 315 measures an ambient temperature of the surrounding atmosphere. The temperature data from the sensors 114, 315 is transmitted to the processor 106 at step 418 via a signal indicative of the reference temperature of the tab 116 and the ambient temperature of the room, respectively.

With the temperature data from the infrared detector 112, the temperature sensor 114, and the ambient sensor 315 received at the processor 106, corrected thermal flux temperatures of the facial region 13 and the tab 116 may be computed by factoring in the ambient temperature. At step 408, the computer readable and executable instructions cause the processor 106 to perform the temperature error correction described above to compute the core temperature ($T_{Core}$) of the subject 12 positioned within the target area 15 by utilizing Equations (4) through (6). In particular, the computer readable and executable instructions 110 cause the processor 106 to calculate a corrected thermal flux of the facial region 13 ($T_{Face}$) and a corrected thermal flux of the tab 116 ($T_{Tab}$). In this instance, the processor 106 computes a difference of the two corrected temperatures ($T_{Face}$, $T_{Tab}$) to arrive at a net temperature value ($T_A$) that equals the temperature difference between the facial region 13 and the tab 116.

The delta ($T_A$) of the detected temperatures (i.e., the difference between the detected temperature of the facial region 13, $T_{Face}$, and the detected temperature of the tab 116, $T_{Tab}$) is combined with the reference temperature of the tab 116, as detected by the temperature sensor 114, to calculate a core temperature of the subject 12 to a relatively greater accuracy. By way of example only, the core temperature is determined with an accuracy of at least ±1.0° Celsius to about ±0.5° Celsius).

At step 420, the core temperature of the subject 12 is compared to the baseline temperature, and an inquiry to determine whether the core temperature of the subject 12 differs from the baseline temperature of the subject 12 (e.g., either greater than the baseline temperature or less than the baseline temperature) by a predetermined threshold. At step 422, an affirmative response to the inquiry of step 420 provides for the initiation of monitoring information in the form of a report/alert signal that is generated by the processor 106. The report/alert signal may be transmitted to an operator via the monitor, for example, the at least one handheld device 190 and/or the at least one remote station 192, to inform an operator of the monitoring system 300 of the subject's core temperature, as detected by the monitoring system 300, and/or to alert an operator of a change in the subject's condition by a predetermined threshold based on the core temperature and the baseline temperature. As described in greater detail above, it should be understood that the predetermined temperature threshold is less than the error range of ±4.0° Celsius of conventional infrared cameras. For example, the predetermined temperature threshold may be about ±1.0° Celsius, and in particular, the threshold may be about ±0.5° Celsius. Alternatively, the inquiry of step 420 may result in a determination that the true temperature of the subject 12 does not exceed the predetermined threshold such that the monitoring system 300 returns to step 404 to perform the system method 400 again at a predetermined interval.

With the incorporation of the infrared detector 112, the temperature sensor 114, the tab 116, and, in some embodiments, the ambient sensor 315, and the methods utilizing the same as described above, the monitoring systems 100, 300 described herein may provide a system capable of improving the temperature detection accuracy of objects positioned within a target area as compared to the temperature error range of conventional infrared imaging systems. In particular, the error range of ±4° Celsius of conventional infrared cameras may be too large to accurately detect meaningful changes in the temperature of a subject 12, such that use of a monitoring system 100, 300 is desirable to increase temperature detection accuracy to an error range of ±2° Celsius, and preferably an error range of ±1° Celsius. With the monitoring system 100, 300 having a smaller error range, an operator of the system may identify changes in a subject's condition in a timelier manner soon after the change has occurred such that earlier care may be provided to the subject than that possible when utilizing conventional monitoring systems.

While embodiments of the monitoring system are described herein in which the first detector utilizes uncooled microbolometer technology, it should be understood that the monitoring system and methods described herein may be utilized with various other imaging devices, cameras, temperature instruments, and the like.

It should now be understood that embodiments described herein are directed to a monitoring system that monitors the core temperature of a subject using an infrared detector, a temperature sensor, and/or a third detector in operable communication with a control unit of the monitoring system. The control unit including a processor that executes operating instructions to compute a temperature of the subject and calibrate the temperature using other temperature data retrieved by the detectors to improve the level of temperature accuracy. The monitoring system may further transmit monitoring information relating to the subject's condition to remote devices/stations for periodic monitoring of the subject's core temperature and/or may generate a report or signal when the subject's core temperature exceeds a predetermined temperature threshold relative to a baseline temperature of the subject. It should be further understood that in other embodiments the monitoring system may include thermal imaging devices that utilize technology other than the uncooled microbolometer technology described above.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A monitoring system, comprising:
   an infrared detector comprising a field of view, the infrared detector detecting temperature data from the field of view and providing a signal indicative of at least a detected temperature of a subject within the field of view;
   a tab comprising a tab temperature, wherein the tab is at least partially positioned within the field of view of the infrared detector such that the infrared detector detects the tab and emits a signal indicative of a detected temperature of the tab;
   a temperature sensor secured to the tab, the temperature sensor detecting the tab temperature and providing a signal indicative of a reference temperature; and
   a control unit communicatively coupled to the infrared detector and the temperature sensor, the control unit comprising a processor and a non-transitory memory device comprising computer readable and executable instructions that, when executed by the processor, cause the control unit to:
   compute a net value between the detected temperature of the subject and the detected temperature of the tab by subtracting the detected temperature of the tab from the detected temperature of the subject; and calculate a core temperature of the subject by combining the computed net value with the reference temperature.

2. The monitoring system of claim 1, wherein the core temperature of the subject calculated by the control unit is within ±0.5° Celsius of an actual temperature.

3. The monitoring system of claim 1, further comprising a remote station, wherein the control unit is coupled to the remote station.

4. The monitoring system of claim 3, wherein the computer readable and executable instructions, when executed by the processor, transmit a signal indicative of the core temperature to the remote station.

5. The monitoring system of claim 4, wherein the remote station receives the signal indicative of the core temperature from the control unit and determines a variance between the core temperature of the subject and a baseline temperature of the subject.

6. The monitoring system of claim 5, wherein the baseline temperature is an initial core temperature determined by the monitoring system and stored in the remote station at initialization of the monitoring system.

7. The monitoring system of claim 5, wherein the baseline temperature is input into the remote station by an operator.

8. The monitoring system of claim 5, wherein the remote station emits an alarm signal when the variance between the core temperature of the subject and the baseline temperature of the subject is greater than a threshold.

9. The monitoring system of claim 8, wherein the alarm signal is transmitted from the remote station to a handheld device.

10. The monitoring system of claim 1, wherein the tab has an emissivity greater than or equal to 0.90.

11. The monitoring system of claim 1, wherein the infrared detector comprises a long wave infrared camera.

12. The monitoring system of claim 1, wherein the infrared detector periodically detects temperature data from the field of view at a predetermined interval and the temperature sensor periodically detects the tab temperature of the tab at the predetermined interval.

13. The monitoring system of claim 1, further comprising an ambient sensor communicatively coupled to the control unit, wherein the ambient sensor is configured to measure an ambient temperature adjacent to the field of view.

14. The monitoring system of claim 13, wherein the computer readable and executable instructions, when executed by the processor, further cause the processor to calibrate the detected temperature of the subject and the detected temperature of the tab based on the ambient temperature.

15. The monitoring system of claim 1, further comprising a baseplate, wherein the tab and the infrared detector are each coupled to the baseplate.

16. A method for monitoring a core temperature of a subject using a system comprising an infrared detector, a temperature sensor, and a tab, the method comprising:
capturing thermal images of a target area with the infrared detector, the target area including the subject and the tab, wherein the thermal images comprise a plurality of pixels corresponding to at least a detected temperature of the subject and a detected temperature of the tab;
measuring a reference temperature of the tab with the temperature sensor positioned on the tab;
determining a difference between the detected temperature of the subject and the detected temperature of the tab from the thermal images by subtracting the detected temperature of the tab from the detected temperature of the subject; and
computing the core temperature of the subject by adding the determined difference to the reference temperature of the tab.

17. The method of claim 16, further comprising initiating an alert in response to the core temperature of the subject exceeding a predetermined threshold, wherein the alert comprises at least one of an audible message, a visual display, and a tactile feedback.

18. The method of claim 16, further comprising calibrating the detected temperature of the subject and the detected temperature of the tab with an ambient temperature of the target area, wherein the ambient temperature is measured by an ambient sensor.

19. A monitoring system comprising:
an infrared detector configured to capture thermal images of a target area;
a tab positioned within the target area such that the infrared detector is configured to capture thermal images of the tab;
a temperature sensor positioned on the tab and configured to measure a temperature of the tab;
an ambient sensor configured to measure an atmospheric temperature adjacent to the target area; and
a processor in communication with the infrared detector, the temperature sensor, and the ambient sensor, the processor configured to:
analyze thermal data from the infrared detector corresponding to a subject within the target area and the tab to detect a temperature of the subject and to detect a temperature of the tab;
analyze thermal data from the temperature sensor corresponding to the tab to detect a reference temperature of the tab;
analyze thermal data from the ambient sensor to detect the atmospheric temperature;
compute a corrected temperature of the subject and a corrected temperature of the tab by calibrating the detected temperature of the subject and the detected temperature of the tab with the atmospheric temperature; and
compute a core temperature of the subject by adding the reference temperature of the tab to a difference between the corrected temperature of the subject and the corrected temperature of the tab, wherein the difference between the corrected temperature of the subject and the corrected temperature of the tab is calculated by subtracting the corrected temperature of the tab from the corrected temperature of the subject.

20. The monitoring system of claim 19, wherein the processor is configured to generate monitoring information relating to the core temperature of the subject, wherein the monitoring information comprises an alert generated in response to the processor determining the core temperature exceeds a predetermined temperature threshold.

* * * * *